United States Patent
Verlaak et al.

(10) Patent No.: US 11,654,231 B2
(45) Date of Patent: May 23, 2023

(54) MEDICAL DEVICE PACKAGING

(71) Applicant: SANOFI, Paris (FR)

(72) Inventors: Stefan Verlaak, Paderno d'Adda (IT); Ilario Melzi, Milan (IT)

(73) Assignee: Sanofi, Paris (FR)

( * ) Notice: Subject to any disclaimer, the term of this patent is extended or adjusted under 35 U.S.C. 154(b) by 1080 days.

(21) Appl. No.: 16/317,001

(22) PCT Filed: Jul. 12, 2017

(86) PCT No.: PCT/EP2017/067511
§ 371 (c)(1),
(2) Date: Jan. 10, 2019

(87) PCT Pub. No.: WO2018/011257
PCT Pub. Date: Jan. 18, 2018

(65) Prior Publication Data
US 2019/0231971 A1    Aug. 1, 2019

(30) Foreign Application Priority Data
Jul. 14, 2016  (EP) .................................... 16305914

(51) Int. Cl.
*A61M 5/00* (2006.01)
*B65D 77/20* (2006.01)
(Continued)

(52) U.S. Cl.
CPC ............. *A61M 5/002* (2013.01); *A61B 50/30* (2016.02); *A61M 5/14248* (2013.01);
(Continued)

(58) Field of Classification Search
CPC ... A61M 5/002; A61M 5/14248; A61B 50/30; A61B 2050/002; A61B 2050/0065;
(Continued)

(56) References Cited

U.S. PATENT DOCUMENTS

| | | | |
|---|---|---|---|
| 6,843,370 B2* | 1/2005 | Tuneberg | A61C 19/02 206/460 |
| 2006/0058599 A1* | 3/2006 | Cummings | A61N 1/0472 600/391 |

(Continued)

FOREIGN PATENT DOCUMENTS

| | | |
|---|---|---|
| CN | 1124918 | 6/1996 |
| CN | 1209073 | 2/1999 |

(Continued)

OTHER PUBLICATIONS

PCT International Preliminary Report on Patentability in International Application No. PCT/EP2017/067511, dated Jan. 15, 2019, 7 pages.

(Continued)

*Primary Examiner* — J. Gregory Pickett
*Assistant Examiner* — Jenine Pagan
(74) *Attorney, Agent, or Firm* — Fish & Richardson P.C.

(57) ABSTRACT

A medical device packaging comprises a container having an opening. A medical device is disposed within the container. The medical device includes an adhesive contact face facing the opening. A first cover is disposed over the opening in the container to close the container. A second cover is disposed over the adhesive contact face of the medical device. The first and second covers are connected such that removal of the first cover from the container causes detachment of the second cover from the medical device.

18 Claims, 5 Drawing Sheets

(51) Int. Cl.
    *B65D 51/18*     (2006.01)
    *A61M 5/142*     (2006.01)
    *A61B 50/30*     (2016.01)
    *A61B 50/00*     (2016.01)

(52) U.S. Cl.
    CPC ....... *B65D 51/185* (2013.01); *B65D 77/2024* (2013.01); *A61B 2050/002* (2016.02); *A61B 2050/0065* (2016.02); *B65D 2251/0031* (2013.01); *B65D 2251/0093* (2013.01)

(58) Field of Classification Search
    CPC .............. B65D 51/185; B65D 77/2024; B65D 2251/0031; B65D 2251/0093
    USPC ................................ 206/363; 220/255, 255.1
    See application file for complete search history.

(56) References Cited

U.S. PATENT DOCUMENTS

2011/0172638 A1* 7/2011 Moga ................. A61M 5/14586
    604/506
2013/0075282 A1* 3/2013 Cinader, Jr. .............. B65B 5/04
    53/471
2014/0034536 A1     2/2014 Reinhardt et al.
2014/0311931 A1* 10/2014 Konishi ............. B65D 83/0835
    206/363
2016/0135895 A1* 5/2016 Faasse ................. B65D 75/326
    53/425

FOREIGN PATENT DOCUMENTS

| | | |
|---|---|---|
| CN | 1726059 | 1/2006 |
| CN | 101460207 | 6/2009 |
| CN | 104302334 | 1/2015 |
| EP | 2650031 | 10/2013 |
| JP | 2009-539444 | 11/2009 |
| JP | 2015-516202 | 6/2015 |
| JP | 2017-526486 | 9/2017 |
| WO | WO 1994/027555 | 12/1994 |
| WO | WO 1997/023252 | 7/1997 |
| WO | WO 2004/041330 | 5/2004 |
| WO | WO 2007/141210 | 12/2007 |
| WO | WO 2013/153039 | 10/2013 |
| WO | WO 2016/041874 | 3/2016 |

OTHER PUBLICATIONS

PCT International Search Report and Written Opinion in International Application No. PCT/EP2017/067511, dated Aug. 8, 2017, 9 pages.

* cited by examiner

MEDICAL DEVICE PACKAGING

CROSS REFERENCE TO RELATED APPLICATIONS

The present application is the national stage entry of International Patent Application No. PCT/EP2017/067511, filed on Jul. 12, 2017, and claims priority to Application No. EP 16305914.0, filed on Jul. 14, 2016, the disclosures of which are incorporated herein by reference.

TECHNICAL FIELD

The present disclosure relates to a medical device packaging.

BACKGROUND

A variety of diseases exist that require regular treatment by injection of a medicament. Injection devices known in the art include infusion and patch pumps for delivering injections of medicament. Another type of injection device is a bolus injector device. Some biological medicaments comprise higher viscosity injectable liquids and are to be administered in larger volumes than traditional liquid medicaments, typically at least 1 ml to a few ml. Some high capacity bolus injectors are called large volume devices (LVDs). Such injection devices may be first supported on a suitable injection site of a patient and, once installed, injection is initiated by the patient or another person (a user).

SUMMARY

In one aspect of the present disclosure, there is provided a medical device packaging comprising a container having an opening, a medical device disposed within the container, the medical device including an adhesive contact face facing the opening, a first cover disposed over the opening in the container to close the container, and a second cover disposed over the adhesive contact face of the medical device, wherein the first and second covers are connected such that removal of the first cover from the container causes detachment of the second cover from the medical device. This may advantageously help towards providing a packaged medical device requiring fewer user preparation steps for use, and facilitating ease of use with lesser likelihood of misuse.

The first and second covers may be connected by a connecting member extending between the first and second covers. This may advantageously help towards causing the removal of the first cover to result in removal of the second cover.

The connecting member may be formed integrally with the second cover. This may advantageously help towards ease and reduced cost of manufacture and reduced manufacturing steps and components.

The connecting member may be secured to the first cover proximate a first edge of the first cover.

The first cover may include a start region unattached to the container to facilitate a user initiating removal of the first cover from the container.

The start region may be disposed at a second edge of the first cover which is on an opposite side of the first cover to the first edge. This may advantageously help towards removal of the second cover occurring only once the first cover is removed or nearly removed.

The container may include a flat rim around the opening and the adhesive contact face of the medical device may be substantially level with the flat rim. This may advantageously help towards facilitating application of the medical device to a patient by handling of the container.

The flat rim may comprise an outwardly-extending flange.

The medical device may be secured within the container. This may advantageously help towards accidental release of dropping of the medical device from within the container once the first and second covers are removed.

The medical device packaging may be configured such that the force required remove the medical device from the container is greater than the force required to detach the second cover from the contact face of the medical device. This may advantageously help towards avoiding the medical device being unintentionally removed from the container by removal of the second cover.

The container may be deformable. This may advantageously help towards affixing the medical device to the patient, and also in removing the medical device from the container. The first and second covers may be configured such that the detachment of the second cover from the medical device is caused sequentially after removal of the first cover from the container. This may advantageously help towards providing a simple and user-friendly packaged medical device and ease of use for the user.

The first and second covers may be configured such that removal of the first cover from the container causes detachment of the second cover from the medical device at least partially simultaneously. This may advantageously help towards providing a simple and user-friendly packaged medical device and ease of use for the user.

The medical device may comprise a medicament injection device containing a reservoir of liquid medicament.

In another aspect, there is provided a method of preparing a medical device packaging for use, the medical device packaging comprising a container having an opening, a medical device disposed within the container and including an adhesive contact face facing the opening, a first cover disposed over the opening in the container to close the container and a second cover disposed over the adhesive contact face of the medical device, the first and second covers being connected, the method comprising removing the first cover from the container and thereby causing detachment of the second cover from the medical device.

The drug delivery process using such injection devices may include numerous steps, including removing one or more device components from their respective packaging, assembly and/or preparation of the components to ready the device for medicament administration and attachment of the injection device to a suitable injection site on the body, before the actual process of injecting the medicament can begin. Some embodiments, may simplify the injection process by reducing the steps a user performs.

BRIEF DESCRIPTION OF THE FIGURES

Embodiments will now be described, by way of example only, with reference to the accompanying drawings, in which.

DETAILED DESCRIPTION

FIGS. 1 to 5 show a medical device packaging 10 according to a first embodiment which comprises a packaging container 11 (hereafter "container 11") having a recess defining an interior space 12. A medical device 13 is received within the interior space 12. The medical device 13 (hereafter "device 13") may be a medicament delivery device such as a medicament injection device, for example an infusion pump, patch pump, a bolus injector device or a LVD. The container 11 includes a flange 14 extending radially outwards around a peripheral edge of the opening of the interior space 12. A container cover 15 is applied over the opening of the container 11 and is bonded to the flange 14 to seal the device 13 within the container 11.

The device 13 includes a contact face 16 (see FIG. 5) which, in use, is placed against a patient's body. The contact face 16 includes an adhesive layer to enable the device 13 to be secured to the patient's body. A device cover 17 is provided over the contact face 16 to cover the adhesive layer thereon before the device is used. The device cover 17 includes a tab 18 extending therefrom. The tab 18 is bonded to an inside surface of the container cover 15 by adhesive 19 or other suitable means. It should be noted that the features shown in FIG. 2, in particular the container and device covers 15, 17, tab 18 and adhesive 19, are not drawn to scale but are of an exaggerated thickness for ease of illustration.

Figure 1:
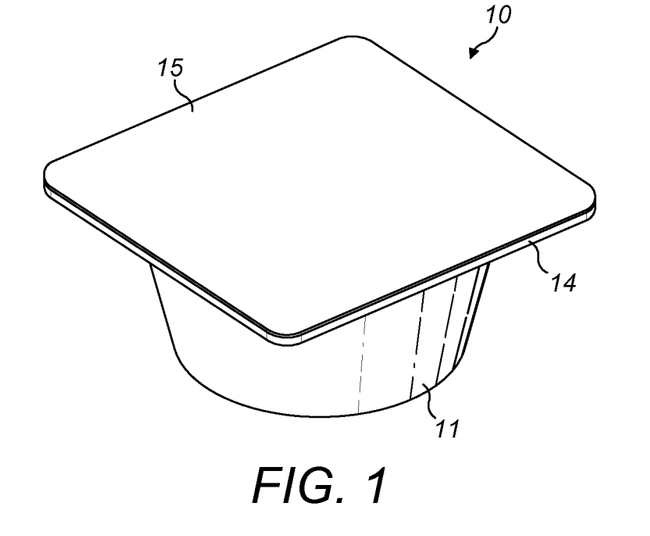
FIG. 1 shows a perspective view of a medical device packaging of a first embodiment, in a sealed state.
Figure 2:
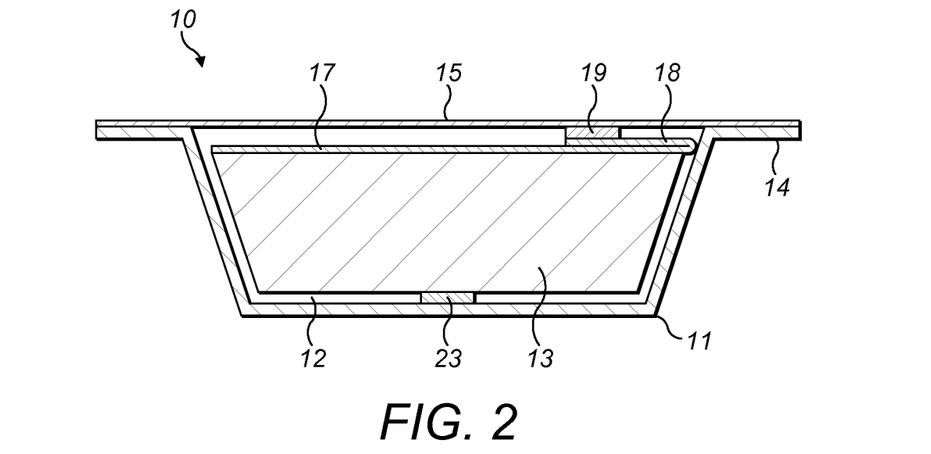
FIG. 2 shows a cross-sectional view of the medical device packaging of FIG. 1.
Figure 3:
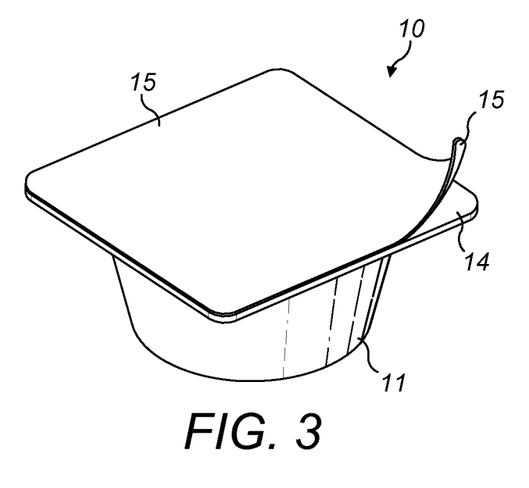
FIG. 3 shows a perspective view of the medical device packaging of FIGS. 1 and 2 in a first partially opened state.
Figure 4:
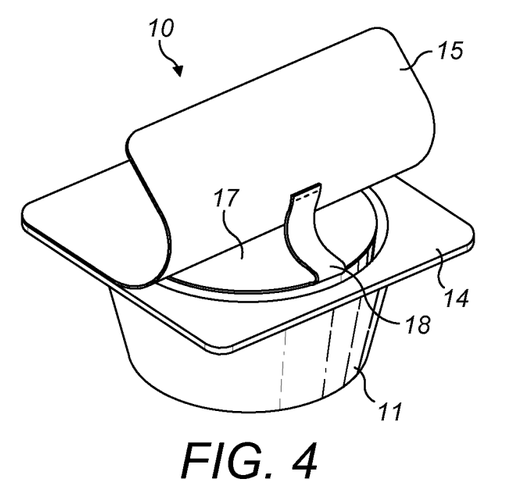
FIG. 4 shows a perspective view of the medical device packaging of FIGS. 1 and 2 in a second partially opened state.
Figure 5:
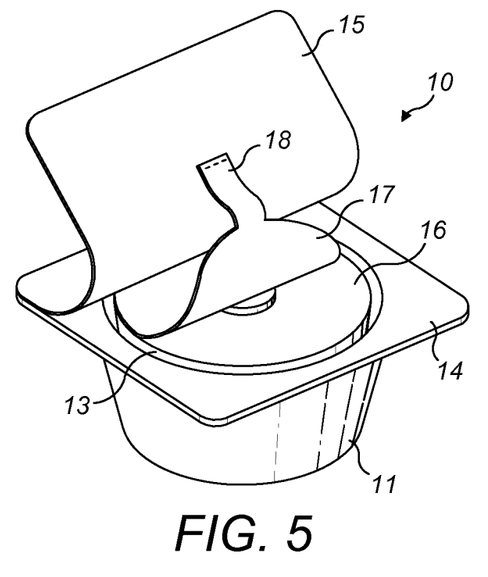
FIG. 5 shows a perspective view of the medical device packaging of FIGS. 1 and 2 in a third partially opened state.

Use of the medical device packaging 10 of the first embodiment will now be described with reference to FIGS. 1 to 7. The medical device packaging 10 is initially in the sealed state as shown in FIGS. 1 and 2. To access the device 13, a user first begins the peel the container cover 15 from the container 11 as shown in FIG. 2. As the user continues to peel the container cover 15 from the container 11, the tab 18 of the device cover 17 is exposed, as shown in FIG. 4. As the user continues to peel the container cover 15 from the container 11, the tab 18 is lifted up with the container cover 15, and the device cover 17 is then peeled away from the contact face 16 of the device 13 in the same movement. The container cover 15 and attached device cover 17 are then fully removed from the container 11 and device 13 respectively and can be discarded.

Figure 6:
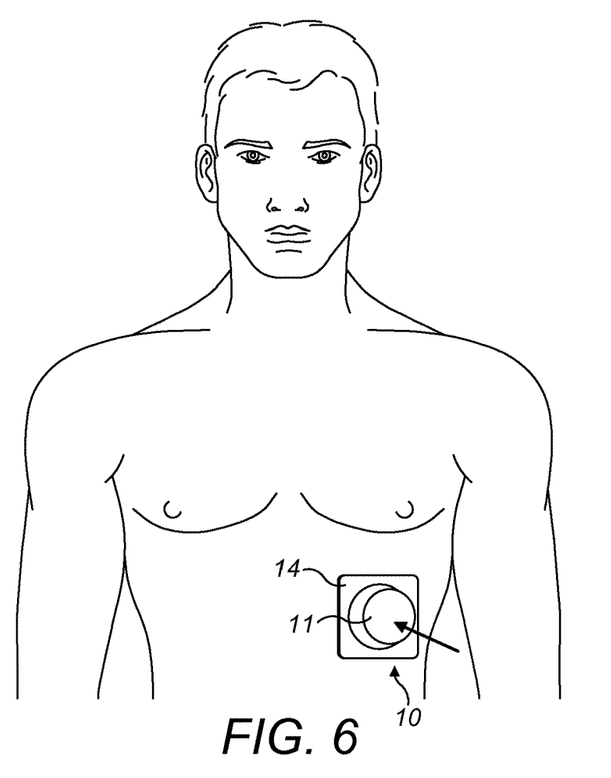
FIG. 6 shows a schematic view of the medical device packaging of FIGS. 1 and 2 being used to apply the medical device to a patient's body.
Figure 7:
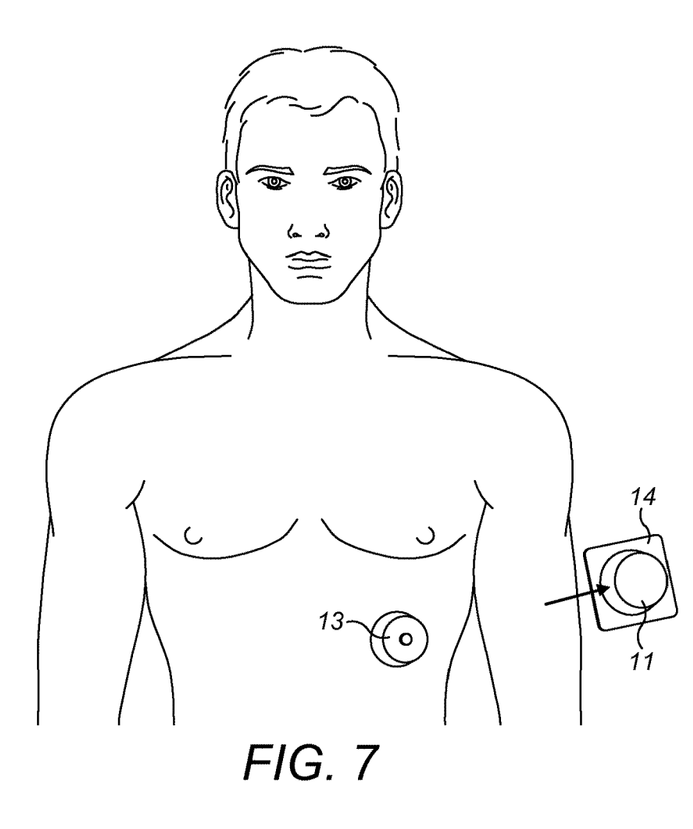
FIG. 7 shows a schematic view similar to that of FIG. 6 once the medical device has been applied to the patient's body and the packaging is removed.

Once the container and device covers 15, 17 are removed, the contact face 16 of the device 13 is exposed in the opening of the container 11. A user can then place the contact face 16 of the device 13 against the intended injection site on the patient's body, whilst the device 13 is still retained within the container 11. This is shown in FIG. 6. The adhesive on the contact face 16 securely attaches the device 13 to the patient's body. The container 11 can then be lifted away from the device 13, leaving the device 13 in place on the patient's body. The container 11 can then be discarded. The device 13 can then be used to administer the medicament in accordance with the manufacturer's instructions.

A medical device packaging 20 of a second embodiment is shown in FIGS. 8A to 8D, and like features in common with the medical device packaging 10 of the first embodiment retain the same reference numerals and a detailed description thereof will not be repeated. A difference of medical device packaging 20 of the second embodiment over that of the first embodiment is that the tab 18 is attached to the container cover proximate an edge portion 21 of the container cover 15. The container cover 15 includes a start region 22 which it is intended the user pulls to initiates the container cover 15 removal process. The start region 22 is at an opposite edge of the container cover 15 to the edge portion 21 proximate to which the tab 18 is attached.

Figure 8A:
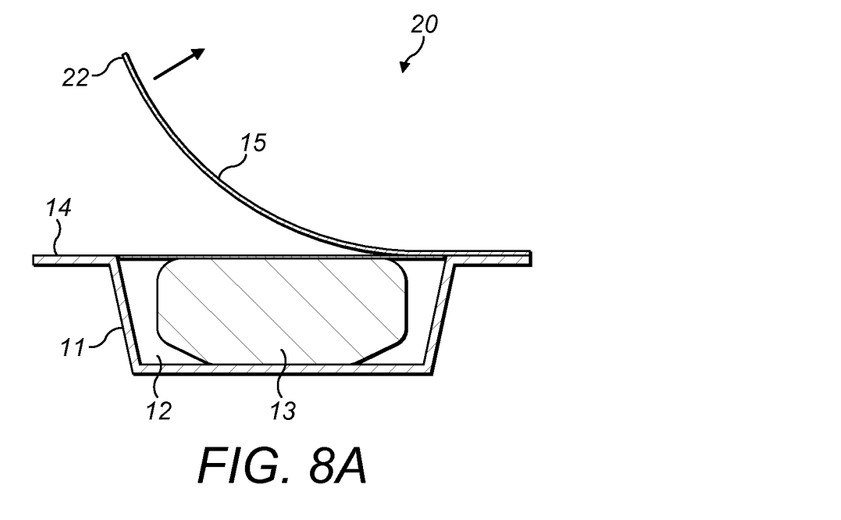
FIGS. 8A to 8D show a series of cross-sectional views of a medical device packaging of a second embodiment, progressively transitioning from a sealed state to an opened state via first and second partially opened states.
Figure 8B:
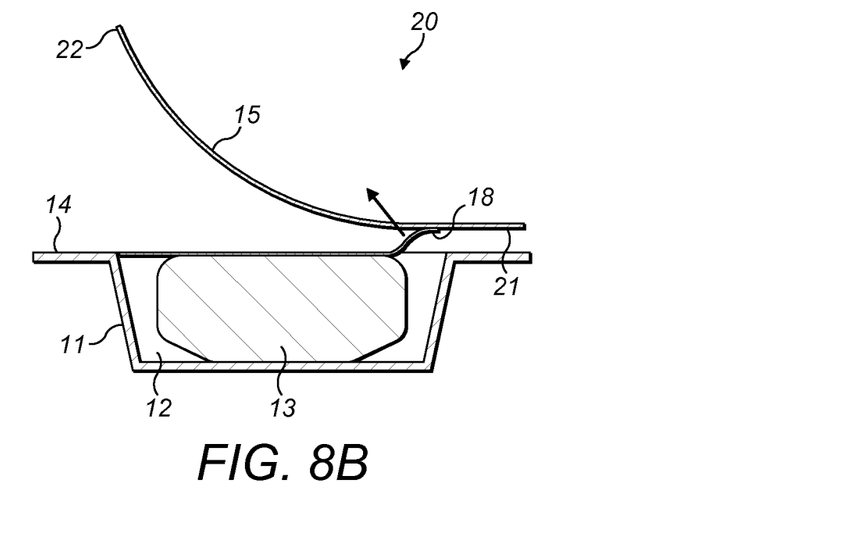
Figure 8C:
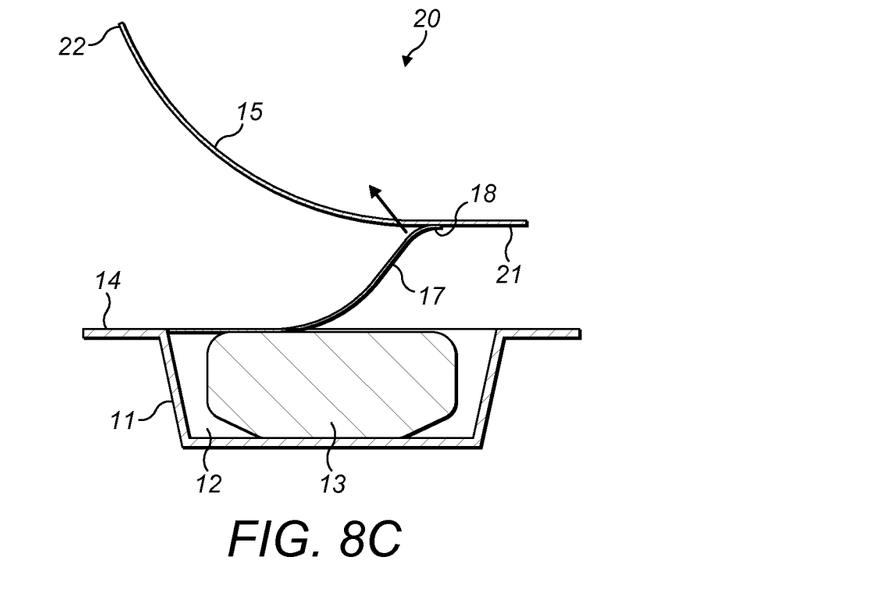
Figure 8D:
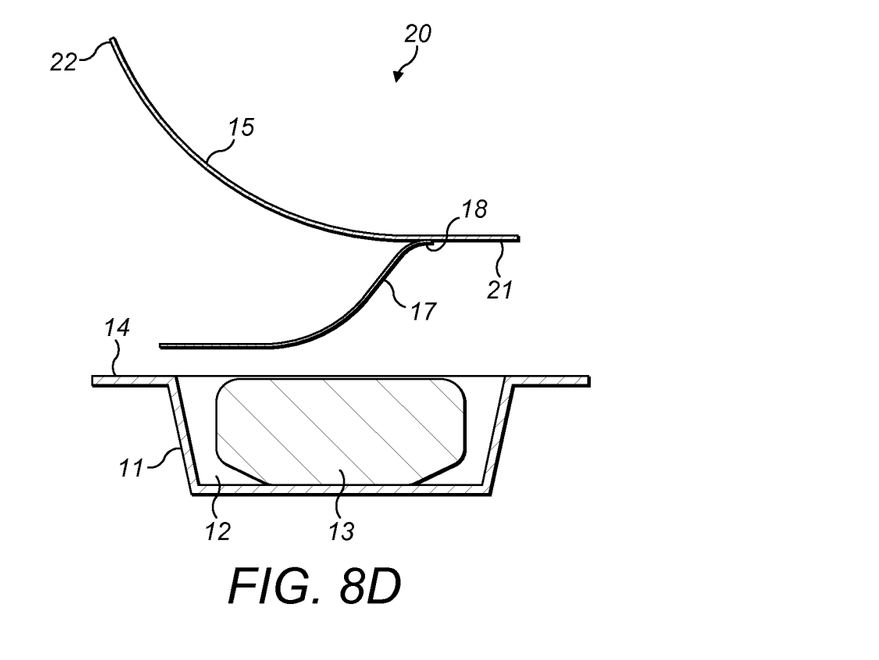

Use of the medical device packaging 20 of the second embodiment will now be described with reference to FIGS. 8A to 8D. The medical device packaging 20 is initially in a sealed state (not shown, but similar to that of the first embodiment shown in FIG. 1). To access the device 13, a user first begins the peel the container cover 15 from the container 11 as shown in FIG. 8A. The user does this by pulling the start region 22 away from the container 11. The user continues to peel the container cover 15 from the container 11 until the container cover 15 is removed up to the opposite side of the container 11 to the start region 22. That is, the container cover 15 is entirely removed from the container 11 as shown in FIG. 8B. At this stage, the container cover 15 is removed from the container 11 and the device cover 17 is still attached to the device. Thereafter, continued pulling of the container cover 15 away from the container 11 pulls the tab 18 away from the device 13 and thereby causes the device cover 17 to be peeled away from the contact face 16 of the device 13. This is shown in FIG. 8C. The peeling of the device cover 17 away from the device 13 progresses in the opposite direction to that which the container cover 15 was peeled away from the container 11. The container cover 15 and the device cover 17 are thereby sequentially removed from the container 11 and device 13 respectively. The container cover 15 and attached device cover 17 are then fully removed from the container 11 and device 13 respectively, as shown in FIG. 8D.

In both embodiments, the contact face 16 of the device 13 may lie substantially flush with the flange 14 of the container 11 when the device 13 is held in the container 11. This is shown in FIGS. 8A to 8D. Although not shown in FIG. 2, this may also be the case with the first embodiment. As mentioned above, the dimensions of the features shown in FIG. 2 are not to scale, for ease of illustration. Having the contact face 16 of the device 13 substantially flush with the flange 14 of the container 11 may enhance ease of application of the device 13 to the patient's body. Alternatively, the contact face 16 of the device 13 may project slightly out of the opening of the container 11 beyond the level of the flange 14 of the container 11. Again, this may enhance ease of application of the device 13 to the patient's body. This may be because once the flange 14 of the container 11 is pressed against the body, the contact face 16 then in contact with the patient's body.

The device 13 may be secured within the container 11. This may be by a non-permanent adhesive 23 (see FIG. 2) or an adhesive patch. This may be provided on a side of the medical device 13 opposite to the contact face 16. This may advantageously retain the device 13 within the container 11 during removal of the device cover 17 from the contact face 16. In such an embodiment, an adhesive 23 holding the device 13 within the container 11 may be configured such that force required to remove the device 13 from the container 11 is greater than the force required to remove the device cover 17 from the contact face 16 of the device 13. This may ensure that the device 13 is not removed from the container 11 when the device cover 17 is being removed from the contact face 16. This may be achieved by selection of adhesives of different bonding strengths, and/or selection of device cover material and its adherence properties with the adhesive on the contact face (16). As an alternative, the container 11 may be configured to hold the device 13 within the container 11. For example, the container 11 may include inward projections or other portions that make frictional contact with the device 13 to grip the device 13 within the container.

An adhesive 23 holding the device 13 within the container 11 may be configured such that force required to remove the device 13 from the container 11 is less than the force required to remove the device 13 from a patient's body once the device 13 is secured thereto by the adhesive on the contact face 16. This may ensure that the device 13 is not detached from the patient's body when the container 11 is removed from the device 13.

The container may be formed of a flexible or deformable material. The material may, for example, comprise plastic, foil, or card. This may enable a user to deform the container 11 to push the device 13 out of the container once the device 13 is secured to the patient's body.

The tab 18 may be integrally formed with device cover 17. This may reduce manufacturing steps as both are formed as a single component. Alternatively, the tab 18 may be a separate component to the device cover 17 and bonded to device and container covers 17, 15. This may be advantageous for the device 13 and device cover 17 to be manufactured in one process and the packaging of the device 13 into the container 11 to form the medical device and package 10, 20, with the tab 18 attached to the container and device cover 15, 17, to be performed in a separate process.

In both embodiments, there may be provided a start region 22 on the container cover 15, which is the intended start point for a user to peel the container cover 15 from the container 11. The start region 22 may not be bonded to flange 14. The start region 22 may include a marker or other graphical indicator to indicate to a user where to pull the container cover 15.

In the first embodiment, the tab 18 is shown attached to the container cover 15 at a location spaced from the edge of the container cover 15. This allows the container cover 15 alone to be initially removed from the container 11 before the device cover 17 begins to be peeled away from the device 13. However, the invention is not intended to be limited to this configuration, and alternatively, the tab 18 may be attached to the container cover 15 at a location proximate to or at the edge of the container cover 15. The tab 18 attachment location may be proximate to or at the start region 22. In such an embodiment, initial pulling of the container cover 15 from the container 11 would immediately, or very shortly afterward, initiate peeling of the device cover 17 from the device 13.

Although the embodiments include a container 11 having a flange 14, extending outwardly from the edge of the container, the invention is not limited to this configuration and the container 11 may not necessarily include such a defined flange, and may alternatively include an edge or rim portion around the opening of the container 11. The container cover 15 may therefore be adhered to the rim or edge of the container opening. The rim or edge may include a flat portion to facilitate the container cover 15 adhering to the container 11. In embodiments having a flange 14, it will be appreciated that the flange 14 provides such a flat portion for adherence of the container cover 15 to the container 11.

Although embodiments described include a tab 18 joining the container and device covers 15, 17, other connecting members may be used within the scope, such as string, thread, wire, material strips. Alternatively, the container and device covers 15, 17 may be otherwise joined together, such as by being bonded at one or more locations on facing surfaces of the container and device covers 15, 17.

It will be appreciated that the inventive concept of the medical device packaging may be applicable to LVDs. However, the invention is not intended to be limited to this particular type of medicament delivery device and the present invention is intended to cover alternative types of medicament delivery devices which include a medicament container to be received in a medicament delivery device which may include, but are not limited to, patch pumps and infusion pumps.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance, which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N—(ω-carboxyheptadecanoyl)-des(B30) human insulin and B29-N—(ω-carboxyhepta¬decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the APIs, substances, formulations, apparatuses, methods, systems and embodiments described herein may be made without departing from the full scope and spirit of the present invention, which encompass such modifications and any and all equivalents thereof.

The invention claimed is:

1. A medical device packaging comprising:
   a container having an opening;
   a medical device disposed within the container, the medical device including an adhesive contact face facing the opening;
   a first cover disposed over the opening in the container to close the container, the first cover comprising a first edge, a second edge opposite the first edge, and a start region disposed at the second edge; and
   a second cover disposed over the adhesive contact face of the medical device,
   wherein the first and second covers are connected such that removal of the first cover from the container causes detachment of the second cover from the medical device to entirely expose the adhesive contact face, and
   wherein the first and second covers are connected proximate the first edge of the first cover.

2. The medical device packaging according to claim 1, wherein the first and second covers are connected by a connecting member extending between the first and second covers.

3. The medical device packaging according to claim 2, wherein the connecting member is formed integrally with the second cover.

4. The medical device packaging according to claim 1, wherein the start region is unattached to the container to facilitate a user initiating removal of the first cover from the container.

5. The medical device packaging according to claim 1, wherein the container includes a flat rim around the opening and the adhesive contact face of the medical device is substantially level with the flat rim.

6. The medical device packaging according to claim 5, wherein the flat rim comprises an outwardly-extending flange.

7. The medical device packaging according to claim 1, wherein the medical device is secured within the container.

8. The medical device packaging according to claim 7, configured such that a force required to remove the medical device from the container is greater than a force required to detach the second cover from the contact face of the medical device.

9. The medical device packaging according to claim 1, wherein the container is deformable.

10. The medical device packaging according to claim 1, wherein the first and second covers are configured such that the detachment of the second cover from the medical device is caused sequentially after removal of the first cover from the container.

11. The medical device packaging according claim 1, wherein the first and second covers are configured such that removal of the first cover from the container causes detachment of the second cover from the medical device at least partially simultaneously.

12. The medical device packaging according to claim 1, wherein the medical device comprises a medicament injection device containing a reservoir of liquid medicament.

13. A method of preparing a medical device packaging for use, the medical device packaging comprising:
   a container having an opening,
   a medical device disposed within the container and including an adhesive contact face facing the opening,
   a first cover disposed over the opening in the container to close the container, the first covering comprising a first edge, a second edge opposite the first edge, and a start region disposed at the second edge, and
   a second cover disposed over the adhesive contact face of the medical device, the first and second covers being connected proximate the first edge of the first cover, the method comprising:
      removing the first cover from the container and thereby causing detachment of the second cover from the medical device to entirely expose the adhesive contact face.

14. The method of claim 13, wherein the first cover is removed from the container before a second container is detached from the medical device.

15. The method of claim 13, wherein the first cover is removed from the container at substantially the same time that a second container is detached from the medical device.

16. The method of claim 13, wherein the medical device comprises a medicament injection device containing a reservoir of liquid medicament.

17. The method of claim 13, wherein the first and second covers are connected by a connecting member extending between the first and second covers.

18. The method of claim 13, wherein a force required to remove the medical device from the container is greater than a force required to detach the second cover from the medical device.

* * * * *

UNITED STATES PATENT AND TRADEMARK OFFICE
CERTIFICATE OF CORRECTION

| | |
|---|---|
| PATENT NO. | : 11,654,231 B2 |
| APPLICATION NO. | : 16/317001 |
| DATED | : May 23, 2023 |
| INVENTOR(S) | : Stefan Verlaak et al. |

It is certified that error appears in the above-identified patent and that said Letters Patent is hereby corrected as shown below:

In the Claims

In Column 10, Line 23, Claim 11, after "according" insert -- to --

Signed and Sealed this
Twenty-ninth Day of August, 2023

Katherine Kelly Vidal
*Director of the United States Patent and Trademark Office*